United States Patent [19]

Krimmer et al.

[11] Patent Number: 4,921,971
[45] Date of Patent: May 1, 1990

[54] METHOD OF PREPARING ALKALINE EARTH METAL SALTS OF 2-PYRROLIDONE-5-CARBOXYLIC ACID

[75] Inventors: Hans-Peter Krimmer, Frankfurt; Karlheinz Drauz, Freigericht; Silvia Werner, Kahl, all of Fed. Rep. of Germany

[73] Assignee: Dequssa Akteingesellschaft, Frankfurt am Main, Fed. Rep. of Germany

[21] Appl. No.: 258,739

[22] Filed: Oct. 17, 1988

[30] Foreign Application Priority Data

Oct. 17, 1987 [DE] Fed. Rep. of Germany ....... 3735264

[51] Int. Cl.$^5$ .......................................... C07D 207/28
[52] U.S. Cl. .................................................. 548/534
[58] Field of Search ......................................... 548/354

[56] References Cited

U.S. PATENT DOCUMENTS 3,235,563 2/1966 Noyori et al. ...................... 548/534
3,243,440 3/1966 Noyori et al. ...................... 548/534

FOREIGN PATENT DOCUMENTS 110559 9/1976 Japan .................................. 548/534

OTHER PUBLICATIONS

Lichtenstein; "Preparation of γ-Alkylamides of Glutamic Acid"; J.A.C.S. 64, pp. 1021–1022 (May '42).
Moeller; *Inorganic Chemistry;* 1976, Wiley & Sons.

*Primary Examiner*—Joseph Paul Brust
*Assistant Examiner*—MarySue Howard
*Attorney, Agent, or Firm*—Cushman, Darby & Cushman

[57] ABSTRACT

Alkaline earth metal salts of 2-pyrrolidone-5-carboxylic acid (pyroglutamic acid) are prepared by heating the corresponding alkaline earth metal salt of glutaminic acid in the solid state to a temperature in a range of 120° C. to 250° C. until the water liberated by the intramolecular condensation (cyclocondensation) has been completely eliminated.

5 Claims, No Drawings

METHOD OF PREPARING ALKALINE EARTH METAL SALTS OF 2-PYRROLIDONE-5-CARBOXYLIC ACID

The present invention relates to a method for the preparation of alkaline earth metal salts of 2-pyrrolidone-5-carboxylic acid of the formula:

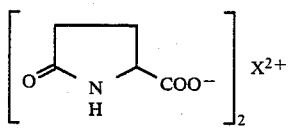 (I)

in which $X^{2+}$ signifies an alkaline earth metal ion.

BACKGROUND OF THE INVENTION

The alkaline earth metal salts of 2-pyrrolidone-5-carboxylic acid are of considerable interest. Thus, for example, magnesium pyroglutamate is used as a pharmaceutical preparation in the treatment of magnesium-deficiency diseases (see Published French Patent Application FR-OS 2,546,064). Calcium pyroglutamate has proven to be an especially useful agent for the replacement of calcium in bone tissue in the case of acute calcium deficiency [E. Moczar, B. Phan Dinh Tuy, L. Robert; "Rhumatologie", Paris, 8, p. 71, (1979)]. Calcium pyroglutamate is also used as corrosion inhibitor in projectile explosives ["Gor. Rep. Announce. Index", USA, 79, p. 227, (1979)].

However, in the past the synthesis of L-calcium pyroglutamates were relatively complicated. For example, the cyclization of a mixture of L-glutamic acid and calcium oxide in aqueous solution at 140° C. and elevated pressure has been described (ES-PS 528,010). A disadvantage of this process is that only an aqueous solution of the calcium pyroglutamate is obtained and that a complete racemization to D,L product occurs. The product used in the pharmaceutical preparations contains only the L-enantiomer, since only the latter is physiologically active.

Another possibility for the preparation of this compound is to react L-pyroglutamic acid with alkaline earth metal hydroxides, oxides or carbonates in water (see published French Patent Application FR-OS 2,546,064); however, only an aqueous solution of the salt is produced in this case as well. Moreover, this process requires the use of L-pyroglutamic acid as a starting material. Pyroglutamic acid is formed by heating L-glutamic acid in concentrated aqueous solution, but the solution is racemized and an equilibrium forms between the starting material and the final product. A further separation step is required for the synthesis of pure L-pyroglutamic acid [see P. M. Hardy, "Synthesis", 1978, p. 290]. The direct heating of L-glutamic acid in the melt to 180° to 185° C. is also accompanied by racemization and, especially, by very strong decomposition [N. Lichtenstein, N. Gertner, "J. Am. Chem. Soc." 64, p. 1021, (1946)].

Finally, the reaction of calcium pyroglutamate with magnesium sulfate has been described for the preparation of magnesium pyroglutamate (French Patent FR-PS M 3593). However, this leaves the problems of synthesis of calcium pyroglutamate which have been described above.

SUMMARY OF THE INVENTION

The present invention provides a method in which a monobasic alkaline earth metal salt of glutamic acid of the formula

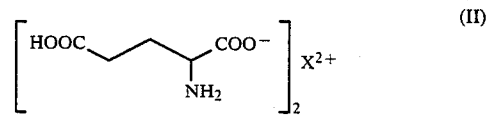 (II)

in which $X^{2+}$ again signifies the corresponding alkaline earth metal ion, is heated, in bulk and in the solid state, to a temperature between 120° C. and 250° C. until the water liberated by the intramolecular condensation has been completely eliminated.

"In bulk" signifies that the reaction is carried out in the absence of any solvent or any other liquid heat-transferring agent.

The heating of the alkaline earth metal salt of formula (II) can take place either discontinuously or continuously, e.g. in a reactor such as an extruder provided with a device for forced transport.

When carrying out the method of the invention, the monobasic alkaline earth metal salts of glutamic acid, which can be obtained very simply from inexpensive glutamic acid and the corresponding alkaline earth hydroxides, oxides or carbonates, are heated in solid form to a temperature between 120° C. and 250° C.

In the case of magnesium glutamate, for example, a temperature of 190° C. has proven to be optimum. A splitting-off of water begins and the formation of magnesium pyroglutamate occurs spontaneously. However, in contrast to the behavior of alkali metal salts of glutamic acid and pyroglutamic acid, no melting occurs during cyclization, that is, even the alkaline earth metal pyroglutamates formed continue to be a solid. Thus, the method of the invention is a solid state reaction. Since the water liberated has a tendency to cause the solid mixture to form clumps of starting material and final product, it is recommended that the latter be constantly agitated during the condensation process and thus remixed. It is also advantageous to carry out the reaction under vacuum since in this manner the water formed is removed more rapidly from the solid mixture. Therefore, a rotary evaporator has proven to be the optimum reaction vessel for rather small to average-sized amounts of material. The rotating boiler of the evaporator dips into an oil bath heated to the optimized temperature and a vacuum of 50 mbars is applied. As soon as the reaction is ended, that is, when no more elimination of water occurs, the product is again quite free-flowing and crystalline and optically indistinguishable from the starting material.

If the temperature of the oil bath is not raised significantly (<20° C.) over the optimized reaction temperature, then no decomposition occurs and also there is no racemization if an enantiomerically pure starting material is used. The reaction, which can be monitored by HPLC analysis, is quantitative. Even with ninhydrin, no more glutamic acid can be found.

The optimized reaction temperatures are slightly different for each alkaline earth metal salt; however, they are all in a range between 170° C. and 220° C. The reaction also occurs as low as 120° C. in the case of magnesium glutamate and calcium glutamate; however, the reaction time increases drastically at this temperature, so that the use of a higher temperature is preferred.

For analytical purposes, a diluted, aqueous solution of the particular alkaline earth metal pyroglutamate can be desalinated via a strongly acidic ion-exchange column (e.g. Duolite C26) and the free pyroglutamic acid is quantitatively obtained after removal of the water under reduced pressure.

All alkaline earth'metal salts of glutamic acid, i.e. the beryllium, magnesium, calcium, strontium and barium salts, can be prepared by the method of the present invention.

The invention is illustrated in more detail in the following examples:

EXAMPLE 1

60 g (0.160 mole) magnesium L-glutamate tetrahydrate were immersed in a 500 ml round flask on a rotary evaporator at a vacuum of 50 mbars partially immersed in an oil bath preheated to 190° C. The elimination of water and the formation of magnesium L-pyroglutamate began after 2 minutes and was completed after 45 minutes. The reaction mixture was a solid at all times during the reaction.

43 g (99.5% of theory) of a colorless powder with a melting point >225° C. were obtained. An HPLC analysis [$NH_2$ column, 3 μm, 250×4.6 mm; mobile solvent: acetonitrile/0.05 M $KH_2PO_4$ (6:4; v/v), UV detector 210 nm] of the product exhibited complete conversion into magnesium L-pyroglutamate. Magnesium L-glutamate could no longer be detected, not even in trace amounts (Rt difference: Mg L-pyroglutamate: Mg L-glutamate approximately 6 minutes).

For conversion into L-pyroglutamic acid, 10 g of the product were dissolved in 100 ml water and passed over an ion-exchange column [Duolite C26, H+ form, (11 cm×2.5 cm; 30 g)]. After elution and removal of the water under reduced pressure, 9 g (quantitative) L-pyroglutamic acid with a melting point of 155°–156° C. were obtained [Cf. H. Gibian, E. Klieger, "Liebigs Ann. Chem." 640, p. 145, (1961): melting point: 156°–157° C.]. $[\alpha]^{25}_D$: −11.8° (c=4, $H_2O$) [Cf. A. C. Kibrick, "J. Biol. Chem." 174, p. 845, 1948: $[\alpha]^{25}_D$: −11.7° (c=4, $H_2O$)].

EXAMPLE 2

10 g (27.16 mmoles) calcium L-glutamate dihydrate were cyclized in the solid state within 20 minutes at a temperature between 150° C. and 170° C. in a manner analogous to Example 1. 8.0 g (99% of theory) calcium L-pyroglutamate were obtained as colorless powder.

EXAMPLE 3

1 g (2.96 mmoles) beryllium L-glutamate dihydrate was cyclized as a solid within 10 minutes at a temperature of 190° C. to 200° C. in a manner analogous to Example 1. 0.75 g (95% of theory) beryllium L-pyroglutamate was obtained.

EXAMPLE 4

1 g (2.4 mmoles) strontium L-glutamate dihydrate was cyclized as a solid within 10 minutes at a temperature of 190° C. to 210° C. in a manner analogous to Example 1. 0.8 g (97% of theory) strontium L-pyroglutamate was obtained.

EXAMPLE 5

5.0 g (10.7 mmoles) barium L-glutamate dihydrate were cyclized as a solid within 20 minutes at a temperature of 200° C. in a manner analogous to Example 1. 4.1 g (97% of theory) barium L-pyroglutamate were obtained as a colorless powder.

What is claimed is:

1. A method for preparing alkaline earth metal salts of 2-pyrrolidone-5-carboxylic acid of the formula

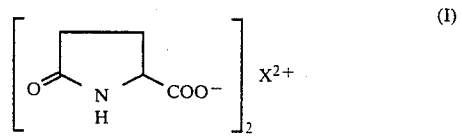

in which $X^{2+}$ signifies an alkaline earth metal ion said method comprising heating a monobasic alkaline earth metal salt of glutamic acid of the formula

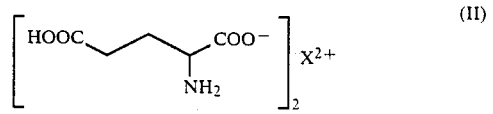

in which $X^{2+}$ signifies the corresponding alkaline earth metal ion in bulk and in the solid state, to a temperature between 120° C. and 250° C. until the water liberated by the intramolecular condensation has been completely eliminated.

2. A method as set forth in claim 1 in which the heating and the elimination of the reaction water takes place discontinuously.

3. A method as set forth in claim 1 in which the heating and the elimination of the reaction water takes place continuously.

4. A method as set forth in any one of claims 1, 2 or 3 in which the heating and the elimination of the reaction water is performed under reduced pressure.

5. A method as set forth in any one of claims 1, 2 or 3 in which the alkaline earth metal salt of glutamic acid is a salt of L-glutamic acid.

* * * * *